US006479553B1

(12) United States Patent
McCarthy

(10) Patent No.: US 6,479,553 B1
(45) Date of Patent: Nov. 12, 2002

(54) USE OF CERTAIN AFFINITY NMDA ANTAGONISTS AS ANTIDEPRESSANTS

(75) Inventor: Dennis J. McCarthy, Shrewsbury, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/554,315

(22) PCT Filed: Mar. 21, 2000

(86) PCT No.: PCT/SE00/00540

§ 371 (c)(1),
(2), (4) Date: May 12, 2000

(87) PCT Pub. No.: WO00/56324

PCT Pub. Date: Sep. 28, 2000

(30) Foreign Application Priority Data

Mar. 23, 1999 (SE) .............................................. 9901077

(51) Int. Cl.[7] ............................................. A61K 31/135
(52) U.S. Cl. ....................................... 514/650; 514/663
(58) Field of Search ................................. 514/650, 663

(56) References Cited

U.S. PATENT DOCUMENTS 5,206,248 A * 4/1993 Smith .......................... 514/289

FOREIGN PATENT DOCUMENTS

EP 0 869 122 A1 10/1998

OTHER PUBLICATIONS

Boireau et al., "The Antidepressant Metapramine is a low–affinity antagonist at N–methyl–D–aspartate acid receptors", Neuropharmacology 35(12), pp. 1703–1707, 1996.*

Abstract to Boireau et al., "The antidepressant metapramine is a low–affinity antagonist at N–methyl–D–aspartic acid receptors", Neuropharmacology 35(12), pp. 1703–1707, 1996.*

Bordier et al, "The Antidepressant Metaprmaine is Low–affinity . . . ," Neuropharmacology, vol. 35, No. 12, pp. 1703–1707 (1996).

* cited by examiner

Primary Examiner—Dwayne C. Jones
(74) Attorney, Agent, or Firm—Nixon & Vanderhye

(57) ABSTRACT

The invention relates to the use of certain pharmaceutical compounds as antidepressant agents.

3 Claims, No Drawings

USE OF CERTAIN AFFINITY NMDA ANTAGONISTS AS ANTIDEPRESSANTS

The present invention relates to the use of certain pharmaceutical compounds as antidepressants.

BACKGROUND OF THE INVENTION

Compounds having NMDA (N-methyl-D-aspartate) antagonist activity are known in the art, for example see Watkins et al., Trends in Pharmacological Science, 11:25, 1990.

In particular, certain compounds are disclosed in EP 279 937 and EP 633 879 as having NMDA antagonist activity and as being useful for treating various CNS disorders such as epilepsy. It has now surprisingly been found that the low affinity NMDA antagonist compounds of EP 633 879 as exemplified by (S)-1-phenyl-2-(2-pyridyl)ethanamine, have activity in the mouse forced swim test, indicating that such compounds are potentially useful as antidepressant agents. In particular, low affinity NMDA antagonists such as (S)-1-phenyl-2-(2-pyridyl)ethanamine are expected to be useful in the treatment of depression associated with neurodegenerative disorders such as Alzheimer's disease. The compound (S)-1-phenyl-2-(2-pyridyl)ethanamine is particularly advantageous in that neither stimulation nor sedation are observed as side effects.

DESCRIPTION OF THE INVENTION

In a first aspect the invention therefore provides the use of a low affinity NMDA antagonist for the treatment of depression.

Particularly suitable compounds include the compounds known as memantine, budipine, amantidine, 5-aminocarbonyl-10,11-dihydro-5H-dibenzo[a,d]cyclohepten-5,10-imine, dextromethorphan and NPS 1506, and the compounds disclosed in EP 279 937 and EP 633 879.

Preferred compounds include compounds of formula (I):

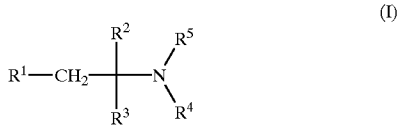

wherein:
$R^1$ is pyridyl, phenyl or 4-fluorophenyl;
$R^2$ is phenyl or 4-fluorophenyl;
$R^3$ is hydrogen, $C_{1-6}$ alkyl or methoxycarbonyl;
$R^4$ is hydrogen or methyl; and
$R^5$ is hydrogen or $COCH_2NH_2$,
and metabolites thereof, both as free bases and pharmaceutically acceptable salts thereof.

Preferably the compound of formula (I) is 1-phenyl-2-(2-pyridyl)ethanamine or a pharmaceutically acceptable salt thereof, more preferably the (S) isomer.

A further preferred compound is 2-amino-N-(1,2-diphenyl-1-methylethyl)acetamide (Remacemide; EP 279 937) or a pharmaceutically acceptable salt or metabolite thereof.

The present invention includes compounds of formula (I) in the form of salts, in particular acid addition salts. Suitable salts include all known pharmaceutically acceptable salts including those formed with both organic and inorganic acids. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids. Hydrochloride salts are particularly preferred.

Substance P antagonists are active in models of depression and may have clinical use in treating depression. Whilst not wishing to be restricted by theory, this implies that Substance P may play a role in the etiology of depression. Substance P is released by stimulation of the NMDA receptor. Therefore, NMDA antagonists may act as antidepressants by inhibition of the release of substance P. Low-affinity use-dependent NMDA antagonists may be particularly effective in treating depression that is associated with diseases such as Alzheimer's disease, Parkinson's disease, stroke, dementia, coronary bypass disease and any other disease in which excitatory amino acids such as glutamate are involved. Therefore the invention also provides a method of treating or preventing depression, including depression associated with the above disorders, which comprises administering to a person in need thereof a therapeutically effective amount of a low affinity NMDA antagonist or a pharmaceutically acceptable salt thereof.

In a further aspect the invention provides a low affinity NMDA antagonist, in particular a compound of formula (I), in the manufacture of a medicament for use in the prevention or treatment of the above disorders, in particular for the treatment or prophylaxis of depression.

Suitable daily dose ranges are from about 0.5 mg/kg to about 5 mg/kg. Unit doses may be administered conventionally once or more than once a day; for example, 2, 3, or 4 times a day; more usually 1 or 2 times a day. A typical dosing regime would be oral, once or twice a day at 30, 60, 120 or 150 mg.

The pharmaceutical composition comprising the compound of the invention may conveniently be tablets, pills, capsules, syrups, powders or granules for oral administration; sterile parental or subcutaneous solutions, suspensions for parental administration; or suppositories for rectal administration; all of which are well known in the art.

EXAMPLE

The following example illustrates the invention.

EXAMPLE

Subjects

The subjects were male NMRI mice (BK Universal, Sollentuna, Sweden), weighing about 25 grams at the time of testing. The mice were housed in groups of 10 per cage under controlled conditions of temperature, relative humidity and light-dark cycle with free access to food and water.

Apparatus

For the forced swim test, the apparatus was a Schott Duran, 2 litre high model, glass beaker, height 23.6 cm, internal diameter 11.8 cm. This beaker was filled with water at a temperature of 25° C. to a depth of 7.5 cm. It was then placed on a bench in front of a mirror.

For the small tube test, the apparatus was an empty 250 ml glass measuring cylinder, with an internal diameter of 3.6 cm.

Procedure

The test compounds were (S)-1-phenyl-2-(2-pyridyl) ethanamine dihydrochloride, (+)-MK 801 (a high affinity NMDA antagonist) and imipramine (a known antidepressant agent).

For both tests, the test solutions were assigned a number from 1 to 5 and tested blind. In each group of 10, two mice were assigned for treatment with each solution. The mice were either injected subcutaneously (s.c) or treated orally (p.o.) at intervals of 6 minutes. Five or 60 minutes after administration, each mouse was placed into the beaker and allowed to swim for 6 minutes (forced swim test).

In a similar manner, in the small tube test, the mouse was placed in the cylinder and allowed to remain there for 6 minutes.

The time spent floating in the beaker or standing still in the measuring cylinder (immobility time) was recorded for the last four minutes of each test using a stopwatch.

Statistics

The length of time spent floating still in each of the last four minutes was subjected to a two-way analysis of variance with one between-subject factor, Treatment, and one within-subject factor, Time. However, in keeping with convention, interactions with the factor Time have not been reported in the results section. Post-hoc comparisons between the treatment groups and control were made using Dunnett's t-test. A significance level of 5% was used throughout.

The results for the forced swim test are shown in Table 1.

TABLE 1

Forced Swim Test in Mice

| Compound Administered (60 minutes pre-test) | Dose (mg/kg i.p.) | Average Immobility Time (seconds) |
|---|---|---|
| None | — | 182 |
| (S)-1-Phenyl-2-(2-pyridyl)ethanamine dihydrochloride | 1 | 158 |
| (S)-1-Phenyl-2-(2-pyridyl)ethanamine dihydrochloride | 3 | 120* |
| (S)-1-Phenyl-2-(2-pyridyl)ethanamine dihydrochloride | 10 | 145* |
| Imipramine | 10 | 143* |
| (+)-MK 801 | 0.01 | 155 |
| (+)-MK 801 | 0.03 | 164 |
| (+)-MK 801 | 0.1 | 80* |
| (+)-MK 801 | 0.3 | 10* |

Results marked with a star (*) are those that were shown to be statistically significant.

Results marked with a star (*) are those that were shown to be statistically significant.

Both the high affinity NMDA antagonist (+)-MK801 and (S)-1-phenyl-2-(2-pyridyl)ethanamine showed positive effects in the forced swim test as indicated by a reduction in immobility time (Table 1). The reference compound imipramine showed a very similar result to that observed with (S)-1-phenyl-2-(2-pyridyl)ethanamine.

As a control procedure to check for non-specific activity in the forced swim test, compounds were further tested in the small tube test. The results for the small tube test are shown in Table 2:

TABLE 2

Small Tube Test in Mice

| Compound Administered (60 minutes pre-test) | Dose (mg/kg i.p.) | Average Immobility Time (seconds) |
|---|---|---|
| None | — | 188 |
| (S)-1-Phenyl-2-(2-pyridyl)ethanamine dihydrochloride | 1 | 192 |
| (S)-1-Phenyl-2-(2-pyridyl)ethanamine dihydrochloride | 3 | 210* |
| (S)-1-Phenyl-2-(2-pyridyl)ethanamine dihydrochloride | 10 | 201 |
| Imipramine | 10 | 202 |
| (+)-MK 801 | 0.01 | 190 |
| (+)-MK 801 | 0.03 | 173 |

TABLE 2-continued

Small Tube Test in Mice

| Compound Administered (60 minutes pre-test) | Dose (mg/kg i.p.) | Average Immobility Time (seconds) |
|---|---|---|
| (+)-MK 801 | 0.1 | 128* |
| (+)-MK 801 | 0.3 | 84* |

Results marked with a star (*) are those that were shown to be statistically significant.

Results marked with a star (*) are those that were shown to be statistically significant.

As can be seen from Table 2, the high affinity NMDA antagonist (+)-MK 801 reduced immobility in the small tube test at the same doses which had an effect in the forced swim test (Table 1). This suggests that the effect of (+)-MK 801 in these tests is due to a non-specific stimulant activity.

In contrast, (S)-1-phenyl-2-(2-pyridyl)ethanamine and the known antidepressant agent imipramine showed little effect in the small tube test, with a trend towards an increase in immobility time (Table 2). Therefore (S)-1-phenyl-2-(2-pyridyl)ethanamine shows the characteristic of an antidepressant agent and does not exhibit stimulant activity.

(S)-1-Phenyl-2-(2-pyridyl)ethanamine was further tested for possible sedative activity in the rat. At doses up to fifty times the oral effective dose in the maximum electroshock seizure test (MES), (S)-1-phenyl-2-(2-pyridyl)ethanamine induced no changes in four parameters of motor activity, namely, distance travelled, ambulatory time, stereotyped time and resting time. The dose administered was 200 mg/kg. These results support the view that at therapeutic doses (S)-1-phenyl-2-(2-pyridyl)ethanamine exhibits neither stimulant nor sedative activity.

What is claimed is:

1. Method of treating or preventing depression in a mammal which comprises administering to a person in need thereof a therapeutic effective amount of a compound having low affinity NMDA antagonist activity or a pharmaceutically acceptable salt thereof, where the compound is a compound of formula (I):

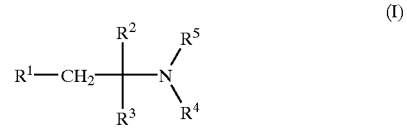

wherein:

R$^1$ is pyridyl, phenyl or 4 fluorophenyl;

R$^2$ is phenyl or 4 flurophenyl;

R$^3$ hydrogen, C$_{16}$ alkyl or methoxycarbonyl;

R$^4$ is hydrogen or methyl; and

R$^5$ is hydrogen or COCH$_2$NH$_2$.

2. Method according to claim 1 wherein the compound of formula (I) is Remacemide or a pharmaceutically acceptable salt or metabolite thereof.

3. Method according to claim 1 wherein the compound of formula (I) is (S)-1-phenyl-2-(2-pyridyl)ethanamine or a pharmaceutically acceptable salt thereof.

* * * * *